United States Patent [19]
Dower et al.

[11] Patent Number: 5,180,812
[45] Date of Patent: * Jan. 19, 1993

[54] SOLUBLE HUMAN INTERLEUKIN-1 RECEPTORS, COMPOSITIONS AND METHOD OF USE

[76] Inventors: Steven K. Dower, Redmond, Wash.; Carl J. March, Bainbridge Island, Wash.; John E. Sims, Seattle, Wash.; David L. Urdal, Seattle, Wash.

[73] Assignee: Immunex Corporation, Seattle, WA

[*] Notice: The portion of the term of this patent subsequent to Jan. 14, 2009 has been disclaimed.

[21] Appl. No.: 455,488

[22] Filed: Dec. 21, 1989

Related U.S. Application Data

[63] Continuation-in-part of Ser. No. 258,756, Oct. 13, 1988, Pat. No. 5,081,228, which is a continuation-in-part of Ser. No. 160,550, Feb. 25, 1988, Pat. No. 4,968,607, which is a continuation-in-part of Ser. No. 125,627, Nov. 25, 1987, abandoned.

[51] Int. Cl.$^5$ ............................................. C07K 13/00
[52] U.S. Cl. ................................... 530/351; 530/350; 530/387.1; 530/395; 424/85.1; 424/85.2; 435/69.5; 435/69.52; 435/69.1; 930/141
[58] Field of Search ............... 530/351, 350, 387, 395; 435/69.5, 69.52, 69.1; 424/85.1, 85.2; 514/2, 8

[56] References Cited

PUBLICATIONS

Van Brunt, *Biotechnolyg*, vol. 7, 1989, p. 668.
Kauokami et al., *Immunology*, vol. 67, 1989, pp. 314-320.
Greenbaum et al., *J. Immunol.* vol. 140, 1988, pp. 1555-1560.
Dower et al., "Detection and Characterization of High Affinity Plasma Membrane Receptors for Human Interleukin 1," *J. Exp. Med.* 162:501-515, 1985.
Dower et al., "Similiarity Between the Interleukin 1 Receptors on a Murine T-Lymphoma Cell Line and on a Murine Fibroblast Cell Lines," *Proc. Natl. Acad. Sci. U.S.A.* 83:1060-1064, 1986.
Kilian et al., "Interleukin-1a and Interleukin 1b Bind to the Same Receptor on T Cells," *J. Immunol.* 136:4509, 1986.
Matsushima et al., "Properties of a Specific Interleukin 1 Receptor on Human Epstein Barr Virus-Transformed . . . " *J. Immunol.* 136:4496, 1986.
Bird et al., "Identification of a Common Class of High Affinity Receptors for Both Types of Porcine Interleukin-1 on Connective Tissue Cells," *Nature* 324:263-266, 1986.
Dower et al., "The Cell Surface Receptors for Interleukin-1a and Interleukin-1b are Identical," *Nature* 324:266-268, 1986.
Chin et al., "Identification of a High-Affinity Receptor for Native Human Interleukin 1b and Interleukin 1a on Normal Human Lung Fibroblasts," *J. Exp. Med.* 165:70-86, 1987.
Mosley et al., "The Interleukin-1 Receptor Binds to the Human Interleukin-1a Precursor but Not the Interleukin-1b Precursor," *J. Biol. Chem* 262:2941-2944, 1987.
Paganelli et al., "Detergent Solubilization of the Interleukin 1 Receptor," *J. Immunol.* 138:2249-2253, 1987.
Dower et al., "The Interleukin-1 Receptor," *Immunology Today* 8:46-51, 1987.
Bron et al., "Identification of the Plasma Membrane Receptor for Interleukin 1 on Mouse Thymoma Cells," *FEBS* 219:365-368, 1987.

(List continued on next page.)

*Primary Examiner*—Garnette D. Draper
*Attorney, Agent, or Firm*—Christopher L. Wight

[57] ABSTRACT

Soluble human Interleukin-1 receptor proteins (shuIL-1Rs) and methods of using shuIL-1Rs to suppress immune or inflamatory responses in a mammal.

2 Claims, 5 Drawing Sheets

Martin et al., "Interleukin 1 Induces Specific Phosphorylation of a 41 Da Plasma Membrane Pritein from the Human Tumor Cell Line K 562," *Immunobiol.* 171:165–169, 1986.

Oppenheim et al., "There is More Than One Interleukin 1," *Immunol. Today* 7:45–56, 1986.

Thieme et al., "Recombinant Murine and Human IL 1a Bind to Human Endothelial Cells with an Equal Affinity, But Have an Unequal Ability to Induce Endothelial Cell Adherence of Lymphocytes," *J. Immunol.* 139:1173–1178, 1987.

Lowenthal et al., "Binding and Internalization of Interleukin 1 by T Cells," *J. Exp. Med.* 164:1060–1074, 1986.

Matsushima et al., "Phosphorylation of a Cytosolic 65-kDa Protein Induced by Interleukin 1 in Glucocorticoid Pretreated Normal Human Peripheral Blood Mononuclear Leukocytes," *J. Immunol.* 139:3367–3374, 1987.

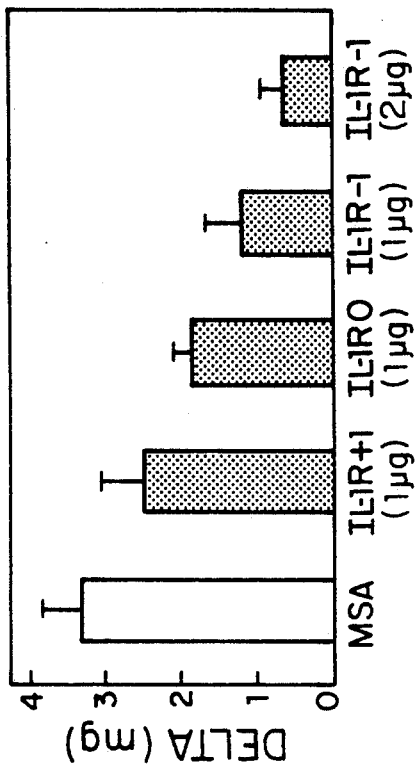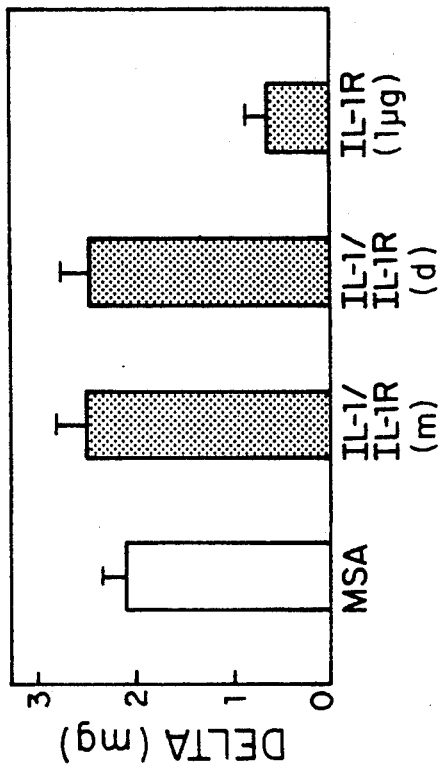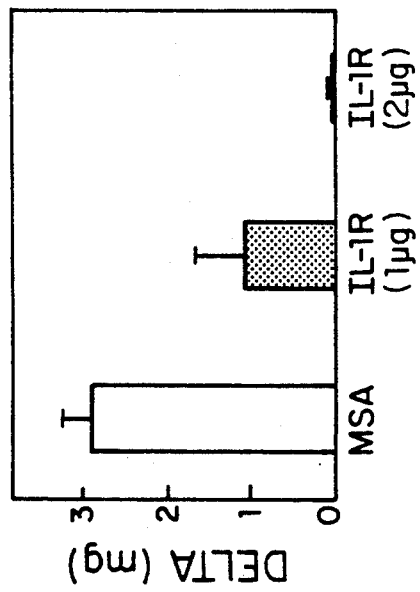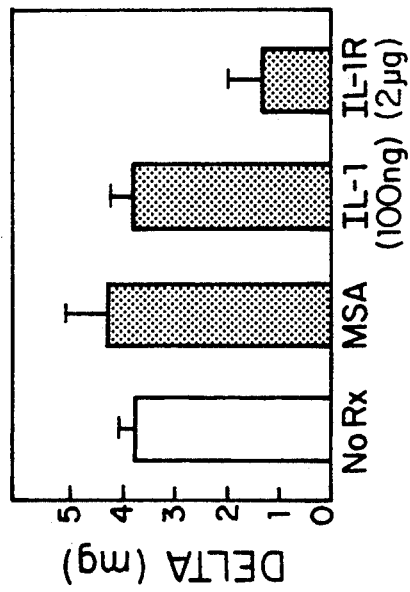

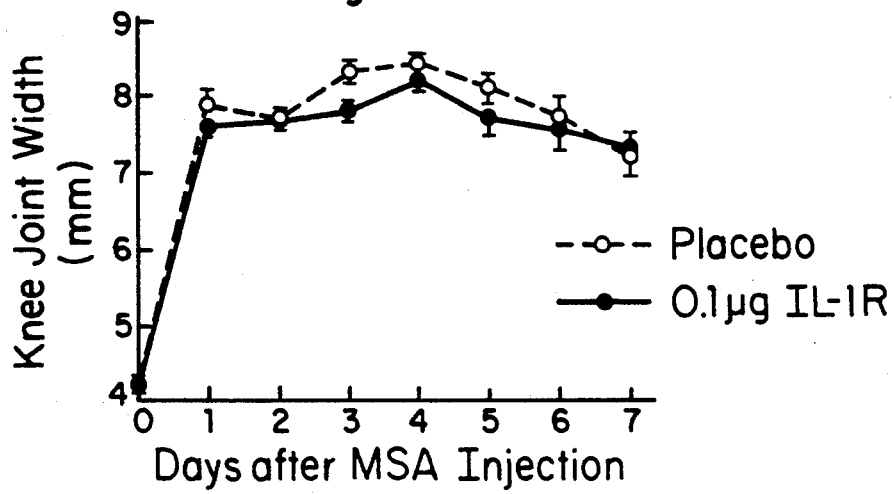
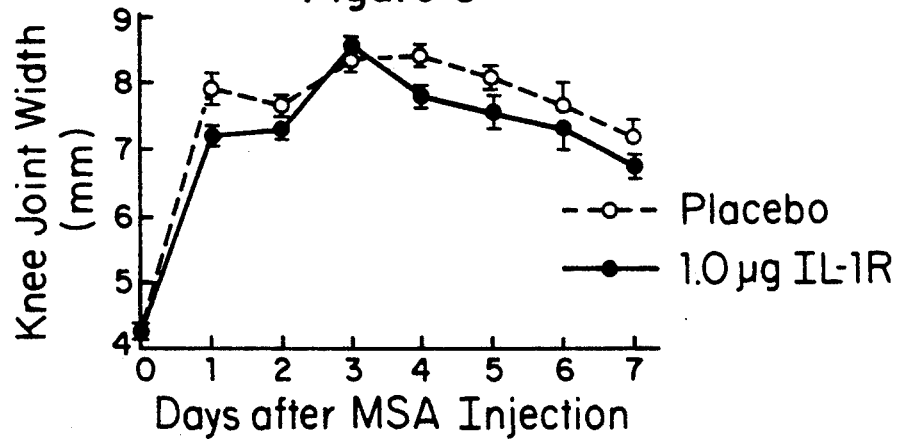
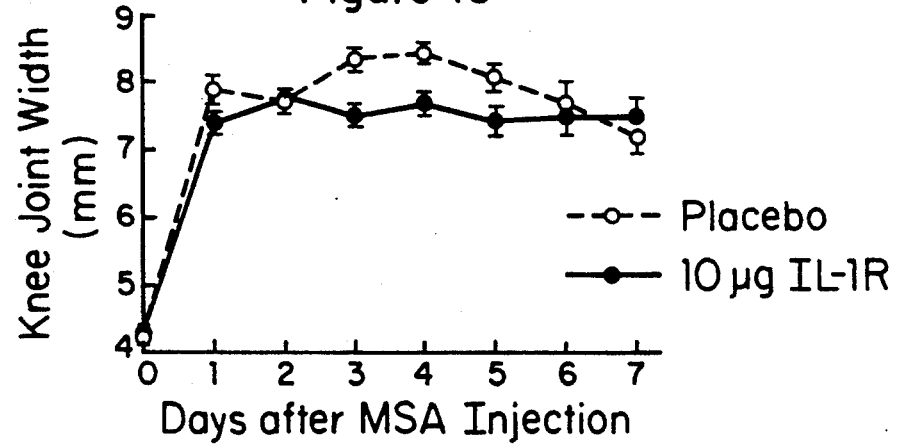

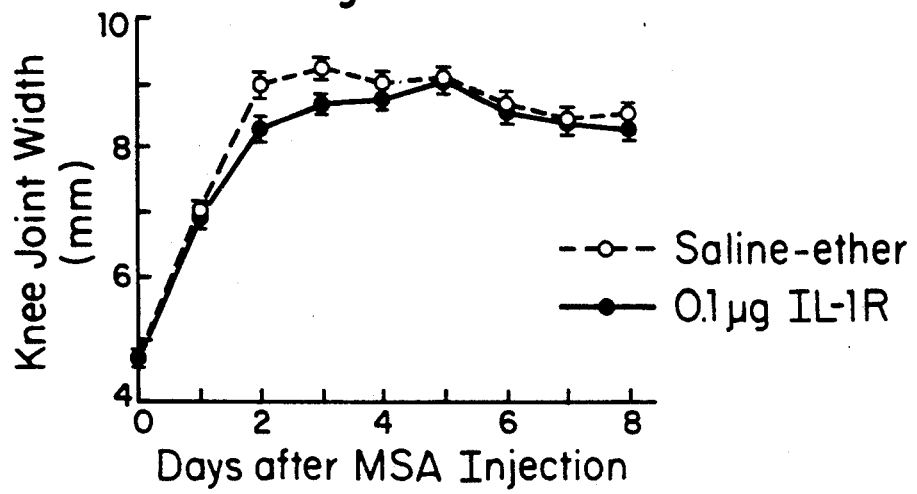
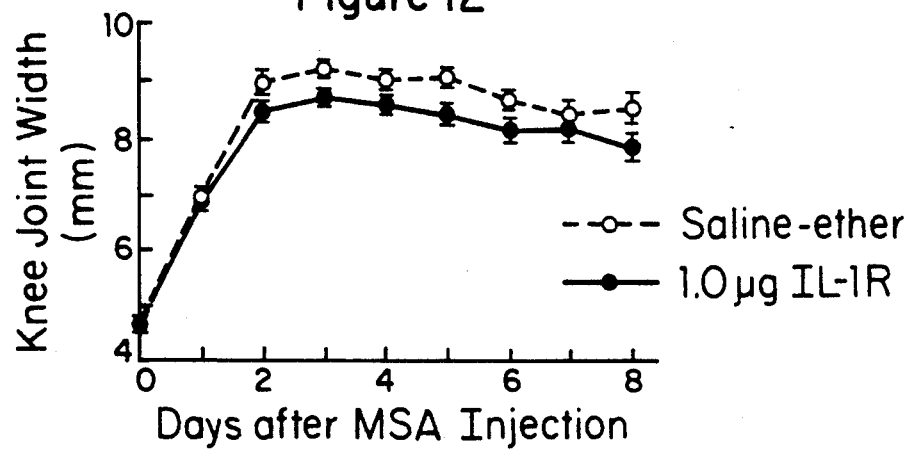
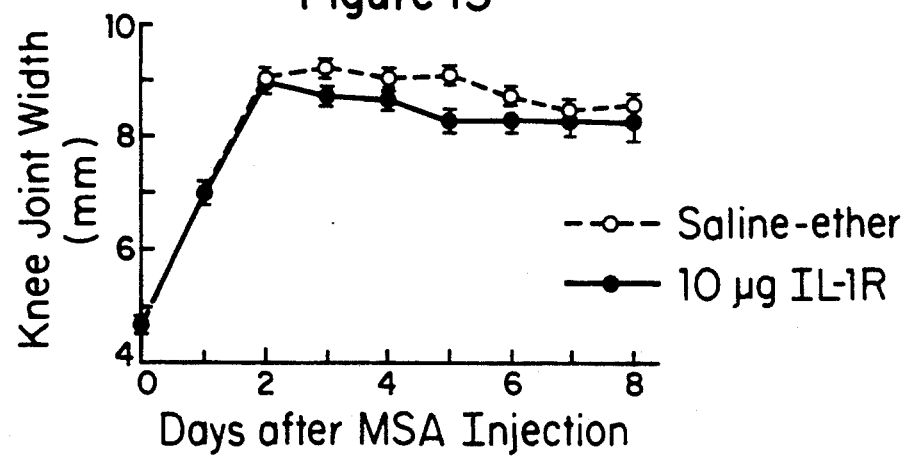

Effect of sol rHu IL-1R on alloantigen induced PLN hypertrophy

A = MSA
B = 100ng sol rHu IL-1R
C = 1000ng sol rHu IL-1R
D = 5000ng sol rHu IL-1R
i.p. day -1, 0, +1

Effect of sol rHu IL-1R on allo-induced lymph node weight gain

SOLUBLE HUMAN INTERLEUKIN-1 RECEPTORS, COMPOSITIONS AND METHOD OF USE

CROSS-REFERENCE TO RELATED APPLICATION

This application is a continuation-in-part of U.S. application Ser. No. 258,756, filed Oct. 13, 1988, now issued as U.S. Pat. No. 5,081,228, which is a continuation-in-part of U.S. application Ser. No. 160,550, filed Feb. 25, 1988, now issued as, U.S. Pat. No. 4,918,607, which is a continuation-in-part of U.S. application Ser. No. 125,627, filed Nov. 25, 1987, now abandoned.

BACKGROUND OF THE INVENTION

The present invention relates generally to cytokine receptor proteins, and more specifically, to soluble truncated interleukin-1 receptor proteins.

Interleukin-1α and interleukin-1β (IL-1α and IL-1β) are distantly related polypeptide hormones which play a central role in the regulation of immune and inflammatory responses. These two proteins were originally both classified as IL-1, based on a shared lymphocyte activation factor (LAF) activity, and a common major cellular source, activated macrophages. As information has accumulated from studies using purified natural and recombinant IL-1 molecules, it has become clear that IL-1α and IL-1β each mediate most, if not all, of the wide range of activities previously ascribed to IL-1.

IL-1α and IL-1β mediate their biological activities via at least two classes of plasma membrane bound receptors. One of these classes of receptor is expressed primarily on T cells and fibroblasts. IL-1α and IL-1β bind to this class of IL-1 receptor, resulting in transduction of a biological signal to various immune effector cells. Because mature full-length IL-1 receptors are bound to the plasma membrane, however, they cannot be effectively used in assay, diagnosis or therapy to regulate immune or inflammatory activities.

SUMMARY OF THE INVENTION

The present invention provides soluble human IL-1 receptor proteins (also referred to herein as shuIL-1R). In preferred embodiments, the invention provides shuIL-1R proteins comprising a polypeptide having the amino acid sequence of residues 1-315 of FIG. 1. Alternative embodiments include proteins having the amino acid sequence of residues 1-316, 1-317, 1-318 or 1-319 of FIG. 1.

The invention also includes compositions for use in suppressing human immune responses, such as lymphoproliferative responses, comprising effective quantities of shuIL-1R proteins.

These and other aspects of the present invention will become evident upon reference to the following detailed description and attached drawings.

BRIEF DESCRIPTION OF THE DRAWINGS

FIGS. 1A and 1B depict the cDNA and amino acid sequences of a preferred shuIL-1R protein. Nucleotide and amino acid residues are numbered from the leucine residue (underline) representing the N-terminus of the mature protein.

FIGS. 2A-2D are graphs showing that smuIL-1R inhibits alloantigen induced proliferation (measured by weight gain) of lymph node cells. Mice are injected in the footpad with syngeneic cells (from the same species) and in the contralateral footpad with allogeneic cells (from another species). Large Δ values (e.g., for MSA or no reaction) indicate that the lymph node draining the site of allogeneic cell deposition (i.e., the treatment failed to inhibit alloantigen induced lymphocyte proliferation and inflammation). Small Δ values indicate that the lymph node draining the site of allogeneic cell deposition did not enlarge (i.e., the treatment inhibited alloantigen induced lymphocyte proliferation and inflammation).

FIGS. 3A-3C are graphs showing the ability of locally administered smuIL-1R to reduce knee joint inflammation from antigen-induced arthritis (AIA).

FIGS. 4A-4C are graphs showing the ability of systemically administered smuIL-1R to reduce knee joint inflammation from AIA.

DETAILED DESCRIPTION OF THE INVENTION

Figure 5:
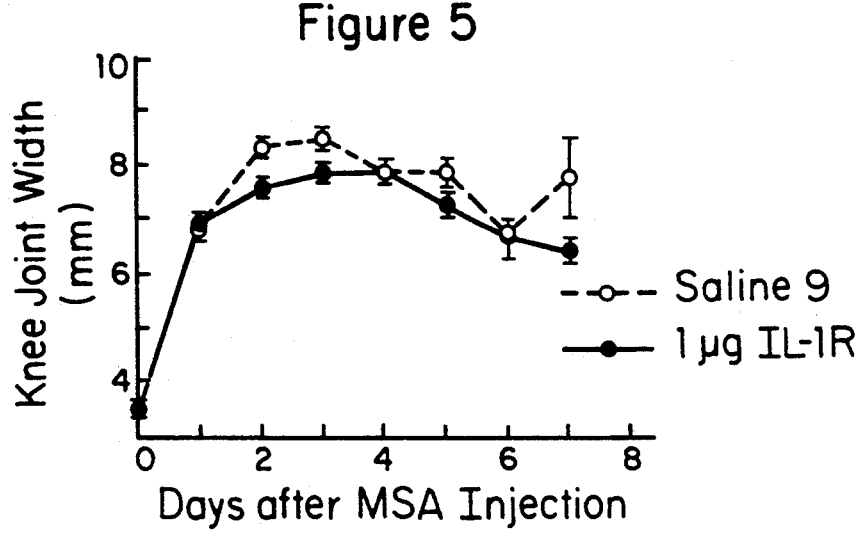
FIGS. 5A-5C are graphs showing the ability of systemically administered smuIL-1R to reduce knee joint inflammation from AIA.

"Interleukin-1 receptor" and "IL-1R" refer to proteins which are capable of binding interleukin-1 (IL-1) molecules and, in their native configuration as intact human plasma membrane proteins, play a role in transducing the signal provided by IL-1 to a cell. Intact receptors generally include an extracellular domain which binds to a ligand, a hydrophobic transmembrane domain which remains embedded within the plasma membrane lipid bilayer, and a cytoplasmic or intracellular domain which is believed to deliver a biological signal to effector cells via a cascade of chemical reactions within the cytoplasm of the cell. The hydrophobic transmembrane domain and a highly charged region of the cytoplasmic domain immediately following the transmembrane domain cooperatively function to halt transport of the IL-1 receptor across the plasma membrane.

"Soluble human IL-1 receptor" or "shuIL-R" means a polypeptide, or a substantially equivalent analog, having an amino acid sequence corresponding to the extracellular region of the native human IL-1 receptor, for example, polypeptides having the amino acid sequences 1-314, 1-315, 1-316, 1-317, 1-318 or 1-319 of FIGS. 1A and 1B. Equivalent shuIL-1Rs include polypeptides which vary from the sequence shown in FIGS. 1A and 1B by one or more amino acid substitutions, deletions, or additions, and which retain the ability to bind IL-1. shuIL-1R proteins lack a transmembrane region and are therefore secreted from recombinant host cells through the plasma membrane.

"Substantially pure", as used in the context of the present invention to define the purity of proteins, refers to soluble human IL-1 receptor compositions free of other human proteins of natural or endogenous origin and containing less than about 1% by mass of protein contaminants residual of production processes. Such compositions, however, can contain other proteins added as stabilizers, carriers, excipients or co-therapeutics.

DNA which codes for sHuIL-1R proteins may be made by constructing cDNAs which encode only the extracellular domain of human IL-1 receptor (devoid of a transmembrane region) using well-known methods of DNA manipulation or mutagenesis. For example, cDNAs which encode shuIL-1R may be constructed by truncating a cDNA encoding the full length IL-1 receptor 5' of the transmembrane region, ligating synthetic oligonucleotides to regenerate truncated portions of the extracellular domain, if desired, and provide a stop codon to terminate transcription.

Isolation of Human cDNA Clones

A 2356 base pair cDNA encoding murine IL-1 receptor was isolated as described by Sims et al., *Science* 241:585, 1988. A murine cDNA probe was then prepared from this cDNA by nick-translation using DNA polymerase I. The probe was used to screen human cDNA libraries for human IL-1R, as described by Sims et al., *Proc. Natl. Acad. Sci.* (USA) 86:8946, 1989.

Briefly, a cDNA library was constructed by reverse transcription of polyadenylated mRNA isolated from total RNA extracted from the cultured cells of a human T-cell line designated clone 22, described by Acres et al., *J. Immunol.* 138:2132, 1987. These cells were cultured in RPMI 1640 medium plus 10% fetal bovine serum as described by Acres et al. (supra), in the presence of 10 ng/ml OKT3 antibody and 10 ng/ml human IL-2. The cDNA was rendered double-standed using DNA polymerase I, blunt-ended with T4 DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., DNA *Cloning: A Practical Approach*, Glover, ed., IRL Press, pp. 49-78). The ligated DNA was packaged into phage particles using a commercially available kit (Stratagene Cloning Systems, San Diego, Calif., USA 92121) to generate a library of recombinants. Recombinants were plated on *E. coli* strain C600(hfl-) and screened by standard plaque hybridization techniques under conditions of moderate stringency (50° C., 6 X SSC).

Following several rounds of screening, nine clones were isolated from the library which hybridized to the cDNA probe. The clones were plaque purified and used to prepare bacteriophage DNA which was digested with EcoRI. The digests were electrophoresed on an agarose gel, blotted onto nylon filters, and retested for hybridization. The clones were digested with EcoRI followed by preparative agarose gel electrophoresis, then subcloned into an EcoRI-cut derivative (pGEMBL) of the standard cloning vector pBR322 containing a polylinker having a unique EcoRI site, a BamHI site and numerous other unique restriction sites. An exemplary vector of this type is described by Dente et al., *Nucl. Acids Res.* 11:1645, 1983.

Restriction mapping and sequencing of a 4.8 kb human IL-1R clone indicated that the clone included a sequence encoding 518 amino acids. A 440 bp EcoRI-NsiI fragment derived from the 5' portion of the human IL-1R clone was $^{32}$P-labeled by nick-translation as described above and used to screen a cDNA library produced by randomly-priming clone 22 mRNA prepared as described above. 23 clones which hybridized to the probe were isolated and analyzed by restriction mapping. Sequencing of one of these clones provided the sequence information corresponding to the remaining N-terminal 34 amino acids of the human protein. The nucleotide sequence of the human IL-1R open reading frame and derived amino acid sequence of the human protein comprises 569 amino acids (including a 17 amino acid signal peptide), including 16 cysteine residues, 13 of which are conserved between the murine and human genes. In addition, the human sequence includes six potential N-glycosylation sites, of which five are conserved between murine and human. The sequence of human IL-1 receptor is set forth in Sims et al., *Proc. Natl. Acad. Sci.* (USA) 86:8946, 1989.

Recombinant Expression Systems shuIL-1R is made by expressing DNA encoding shuIL-1R in a recombinant transcriptional unit under the control of mammalian, microbial, or viral transcriptional or translational control elements. For example, a sequence to be expressed in a microorganism will contain no introns. In preferred aspects, DNA sequences are derived from cDNA sequences. Such sequences may be linked or flanked by DNA sequences prepared by assembly of synthetic oligonucleotides. However, synthetic genes assembled exclusively from oligonucleotides could be constructed using the sequence information provided herein. Alternatively, the coding sequences may include codons encoding one or more additional amino acids located at the N-terminus, for example, an N-terminal ATG codon specifying methionine linked in reading frame with the nucleotide sequence. Due to degeneracy of the genetic code, more than one nucleotide codon can code for a given amino acid; nucleotide sequences which encode soluble human IL-1R can therefore vary considerably. Amino acid sequences encoded by nucleotide sequences which are capable of hybridizing to the sequence of nucleotides disclosed in FIG. 1 under moderately stringent conditions (50° C., 2 X SSC) or which are degenerate to those described above, and which are capable of binding IL-1, are equivalent to those specifically described herein.

The DNA vectors for producing useful quantities of purified shuIL-1R can comprise synthetic or cDNA-derived DNA fragments encoding shuIL-1R or bioequivalent homologues operably linked to regulatory elements derived from mammalian, bacterial, yeast, bacteriophage, or viral genes. Useful regulatory elements are described in greater detail below. Following transformation, transfection or infection of appropriate cell lines, such vectors can be induced to express recombinant protein.

shuIL-1Rs can be expressed in mammalian cells, yeast, bacteria, or other cells under the control of appropriate promoters. Cell-free translation systems could also be employed to produce sHuIL-1R using RNAs derived from the DNA constructs of the present invention. Appropriate cloning and expression vectors for use with bacterial, fungal, yeast, and mammalian cellular hosts are described by Pouwels et al., *Cloning Vectors: A Laboratory Manual*, Elsevier, N.Y., 1985, the relevant disclosure of which is hereby incorporated by reference.

Various mammalian cell culture systems can be employed to express recombinant protein. Examples of suitable mammalian host cell lines include the COS-7 lines of monkey kidney cells, described by Gluzman, *Cell* 23:175, 1981, and other cell lines capable of expressing an appropriate vector, for example, the C127, 3T3, CHO, HeLa, NS1, BHK and myeloma type cell lines. Mammalian expression vectors may comprise nontranscribed elements such as an origin of replication, a suitable promoter and enhancer, and other 5' or 3' flanking nontranscribed sequences, and 5' or 3' nontranslated sequences, such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Additional details regarding the use of a mammalian high expression vector to produce a recombinant shuIL-1R are provided in Examples 1-3 below. Exemplary vectors can be constructed as disclosed by Okayama and Berg, *Mol. Cell. Biol.* 3:280, 1983.

A useful system for stable high level expression of mammalian receptor cDNAs in C127 murine mammary epithelial cells can be constructed substantially as described by Cosman et al., *Mol. Immunol.* 23:935, 1986.

Yeast systems, preferably employing Saccharomyces species such as *S. cerevisiae*, can also be employed for expression of the recombinant proteins of this invention. Yeast of other genera, for example, Pichia or Kluyveromyces, have also been employed as production strains for recombinant proteins.

Generally, useful yeast vectors will include origins of replication and selectable markers permitting transformation of both yeast and *E. coli*, e.g., the ampicillin resistance gene of *E. coli* and *S. cerevisiae* TRP1 gene, and a promoter derived from a highly-expressed yeast gene to induce transcription of a downstream structural sequence. Such promoters can be derived from yeast transcriptional units encoding highly expressed genes such as 3-phosphoglycerate kinase (PGK), $\alpha$-factor, acid phosphatase, or heat shock proteins, among others. The heterologous structural sequence is assembled in appropriate reading frame with translation initiation and termination sequences, and, preferably, a leader sequence capable of directing secretion of translated protein into the extracellular medium.

Useful yeast vectors can be assembled using DNA sequences from pBR322 for selection and replication in *E. coli* (Amp$^r$ gene and origin of replication) and yeast DNA sequences including a glucose-repressible alcohol dehydrogenase 2 (ADH2) promoter. The ADH2 promoter has been described by Russell et al., *J. Biol. Chem.* 258:2674, 1982, and Beier et al., *Nature* 300:724, 1982. Such vectors may also include a yeast TRP1 gene as a selectable marker and the yeast $2\mu$ origin of replication. A yeast leader sequence, for example, the $\alpha$-factor leader which directs secretion of heterologous proteins from a yeast host, can be inserted between the promoter and the structural gene to be expressed (see Kurjan et al., U.S. Pat. No. 4,546,082; Kurjan et al., *Cell* 30:933, 1982; and Bitter et al., *Proc. Natl. Acad. Sci. USA* 81:5330, 1984). The leader sequence may be modified to contain, near its 3' end, one or more useful restriction sites to facilitate fusion of the leader sequence to foreign genes.

Suitable yeast transformation protocols are known to those skilled in the art; an exemplary technique is described by Hinnen et al., *Proc. Natl. Acad. Sci. USA* 75:1929, 1978, selecting for TRP$^+$ transformants in a selective medium consisting of 0.67% yeast nitrogen base, 0.5% casamino acids, 2% glucose, 10 $\mu$g/ml adenine and 20 $\mu$g/ml uracil.

Host strains transformed by vectors comprising the ADH2 promoter may be grown for expression in a rich medium consisting of 1% yeast extract, 2% peptone, and 1% glucose supplemented with 80 $\mu$g/ml adenine and 80 $\mu$g/ml uracil. Derepression of the ADH2 promoter occurs upon exhaustion of medium glucose. Crude yeast supernatants are harvested by filtration and held at 4° C. prior to further purification.

Useful expression vectors for bacterial use are constructed by inserting a DNA sequence encoding sHuIL-1R together with suitable translation initiation and termination signals in operable reading phase with a functional promoter. The vector will comprise one or more phenotypic selectable markers and an origin of replication to ensure replication within the host. Suitable prokaryotic hosts for transformation include *E. coli*, *Bacillus subtilis*, *Salmonella typhimurium*, and various species within the genera Pseudomonas, Streptomyces, and Staphylococcus, although others may also be employed as a matter of choice.

Expression vectors are conveniently constructed by cleavage of cDNA clones at sites close to the codon encoding the N-terminal residue of the mature protein. Synthetic oligonucleotides can then be used to "add back" any deleted sections of the coding region and to provide a linking sequence for ligation of the coding fragment in appropriate reading frame in the expression vector, and optionally a codon specifying an initiator methionine.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

A particularly useful bacterial expression system employs the phage $\lambda$ phage P$_L$ promoter and cI857 thermolabile repressor. Plasmid vectors available from the American Type Culture Collection which incorporate derivatives of the $\lambda$ phage P$_L$ promoter include plasmid pHUB2, resident in *E. coli* strain JMB9 (ATCC 37092) and pPLc28, resident in *E. coli* RR1 (ATCC 53082). Other useful promoters for expression in *E. coli* include the T7 RNA polymerase promoter described by Studier et al., *J. Mol. Biol.* 189: 113, 1986, the lacZ promoter described by Lauer, *J. Mol. Appl. Genet.* 1:139-147, 1981, and available as ATCC 37121, and the tac promoter described by Maniatis, *Molecular Cloning: A Laboratory Manual*, Cold Spring Harbor Laboratory, 1982, p 412, and available as ATCC 37138.

Following transformation of a suitable host strain and growth of the host strain to an appropriate cell density, the selected promoter is derepressed by appropriate means (e.g., temperature shift or chemical induction) and cells cultured for an additional period. Cells are typically harvested by centrifugation, disrupted by physical or chemical means, and the resulting crude extract retained for further purification. Cells are grown, for example, in a 10 liter fermenter employing conditions of maximum aeration and vigorous agitation. An antifoaming agent (for example, polyethylene glycol) is preferably employed. Cultures are grown at 30° C. on appropriate production medium, for example, superinduction medium disclosed by Mott et al., *Proc. Natl. Acad. Sci.* USA 82:88, 1985. Glucose may be added to feed the cultures during the fermentation.

Production is initiated by derepression during exponential phase growth by elevating the temperature to 42° C., and harvested from 2–20, preferably 3–6, hours after the upward temperature shift. The cell mass is initially concentrated by filtration or other means, then centrifuged at 10,000×g for 10 minutes at 4° C. followed by either immediate purification or storage by rapid freezing of the cell pellet.

Purification Processes

Preferably, purified shuIL-1Rs or bioequivalent homologues are prepared by culturing suitable host/vector systems to express the recombinant translation products of the synthetic genes encoding proteins of the present invention. The proteins are then purified from cell culture media.

Media can be optionally concentrated using a commercially available protein concentration filter, for example, an Amicon or Millipore Pellicon ultrafiltration unit. Following the concentration step, the concentrate can be applied to a suitable purification matrix as previously described. For example, a suitable affinity matrix can comprise an IL-1 or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify an IL-1R composition. Some or all of the foregoing purification steps, in various combinations, can also be employed to provide a substantially pure recombinant protein.

Recombinant protein produced in bacterial culture is usually isolated by initial extraction from cell pellets, followed by one or more concentration, salting-out, hydrophobic interaction chromatography (HIC), aqueous ion exchange or size exclusion chromatography steps. Finally, high performance liquid chromatography (HPLC) can be employed for final purification steps. Microbial cells employed in expression of recombinant shuIL-1R can be disrupted by any convenient method, including freeze-thaw cycling, sonication, mechanical disruption, or use of cell lysing agents.

Fermentation of yeast which express shuIL-1R as a secreted protein greatly simplifies purification. Secreted recombinant protein resulting from a large-scale fermentation can be purified by methods analogous to those disclosed by Urdal et al., *J. Chromatog.* 296:171, 1984. This reference describes two sequential, reversed-phase HPLC steps for purification of recombinant human GM-CSF on a preparative HPLC column. Preferably, aqueous ion exchange purification, HIC, affinity purification or IL-1 induced selective precipitation is employed.

Equivalent Protein Analogs

In its various embodiments, the present invention provides substantially pure recombinant shuIL-1R polypeptides free of contaminating endogenous materials, with or without associated native-pattern glycosylation. shuIL-1R expressed in mammalian expression systems, e.g., COS-7 cells, may be similar or slightly different in molecular weight and glycosylation pattern to corresponding molecules expressed in other other expression systems.

Recombinant shuIL-1R proteins within the scope of the present invention also include N-terminal methionyl IL-1Rs. shuIL-1R can also be expressed as a fusion protein with homopolymeric tails of arginine or histidine or other highly charged polypeptide segments to facilitate expression in microorganisms or purification of microbially expressed proteins. For example, purification of heterologously produced shuIL-1R can be facilitated by fusing shuIL-1R to a polyhistidine segment comprising two to six histidine residues, either at the amino terminus or at the carboxy terminus of the soluble receptor. The shuIL-1R/polyhistidine fusion protein is purified with a methal chelate adsorbent, such as iminodiacetic acid (IDA), N.N.N′-tris(carboxymethyl)ethylenediamine (TED) or nitrilotriaceitic acid (NTA) bound covalently to a carrier matrix, such as oxirane-activated agarose, which is then charged with metal ions such as $Cu^{2+}$, $Zn^{2+}$ or $Ni^{2+}$. One particularly preferred nickel chelate affinity chromatography purification scheme which has a high selectivity for polyhistitidine residues even in the presence of high concentrations of guanidinium hydrochloride is described by Hochuli et al., *Bio/Technology* 6:1321, 1988.

In another embodiment of the present invention, the amino acid sequence of sHuIL-1R may be fused to an N-terminal peptide Asp-Tyr-Lys-Asp-Asp-Asp-Asp-Lys (DYKDDDDK). The latter sequence is highly antigenic and provides an epitope reversibly bound by specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in E. coli. An alternative construction is Asp-Tyr-Lys-Asp-Asp-Asp-Lys-Glu-Ile-Gly-Arg, which provides a Factor X recognition site immediately downstream from the enterokinase site. Details of the construction and use of such fusion proteins is disclosed in U.S. Pat. Nos. 4,703,004; 4,782,137, and 4,851,341.

Bioequivalent homologues of the proteins of this invention include various analogs, for example, those in which one or more cysteine residues have been deleted or replaced with other amino acids, for example, neutral amino acids. Other approaches to mutagenesis involve the modification of the protein sequence to eliminate one or more N-linked glycosylation sites to preclude covalent bonding of oligosaccharide moieties to particular amino acid residues by the cell.

Expression in yeast can be enhanced by using site-specific mutagenesis procedures to alter adjacent dibasic amino acid residues which are susceptible to proteolytic cleavage by the KEX2 protease cleavage of *S. cerevisiae*. KEX2 protease processing sites are altered by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The resulting analogs are less susceptible to cleavage by the KEX2 protease at locations other than the yeast α-factor leader sequence, where cleavage upon secretion is intended. KEX2 protease processing sites are found in shuIL-1R at amino acids 270-271 (Lys-Arg) and 271-272 (Arg-Arg) of FIG. 1B.

Biologically active, homogeneous analogs of immuno-regulatory glycoproteins having reduced carbohydrate may be desirable for therapeutic use. Functional mutant analogs of shuIL-1R having inactivated N-glycosylation sites can be produced by oligonucleotide synthesis and ligation or by site-specific mutagenesis techniques as described below. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$. Preferably, substitutions are made conservatively; i.e., the most preferred substitute amino acids are those having physicochemical characteristics resembling those of the residue to be replaced. Similarly, when a deletion or insertion strategy is adopted, the potential effect of the deletion or insertion upon biological activity should be considered.

In addition to the particular analogs described above, numerous DNA constructions including all or part of the nucleotide sequence 1-315 depicted in FIG. 1A and 1B, in conjunction with oligonucleotide cassettes comprising additional useful restriction sites, can be prepared as a matter of convenience. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, addition or deletion.

Alternatively, oligonucleotide-directed site-specific mutagenesis procedures can be employed to provide an altered gene having particular codons altered according to the substitution, deletion, addition or insertion required. By way of example, Walder et al., *Gene* 42:133, 1986; Bauer et al., *Gene* 37:73, 1985; Craik, *Biotechniques*, January 1985, 12–19; Smith et al., *Genetic Engineering: Principles and Methods*, Plenum Press, 1981; and U.S. Pat. No. 4,518,584 disclose suitable techniques, and are incorporated by reference herein.

In another preferred embodiment of the present invention, shuIL-1R is fused to the Fc portion of immunoglobulin, thereby prolonging the in vivo half-life of the receptor molecule.

Administration of Soluble Human IL-1R

In composition and method of use aspects, the present invention provides therapeutic compositions comprising an effective amount of shuIL-1R proteins and a suitable diluent and carrier, and methods for suppressing IL-1-dependent immune responses in humans comprising administering an effective amount of shuIL-1R protein. Use in conjunction with other soluble cytokine receptors, e.g., IL-4 receptor, is also contemplated.

For therapeutic use, purified shuIL-1R protein is administered to a human for treatment in a manner appropriate to the indication. Thus, for example, shuIL-1R protein compositions administered to suppress immune function can be given by bolus injection, continuous infusion, sustained release from implants, or other suitable technique. Typically, a shuIL-1R therapeutic agent will be administered in the form of a composition comprising purified protein in conjunction with physiologically acceptable carriers, excipients or diluents. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials; generally, shuIL-1R dosages of from about 1 ng/kg/day to about 10 mg/kg/day, and more preferably from about 500 μg/kg/day to about 5 mg/kg/day, are expected to induce a biological effect.

shuIL-1R proteins can be administered, for example, for the purpose of suppressing immune responses in a human. A variety of diseases or conditions are caused by an immune response to alloantigen, including allograft rejection and graft-versus-host reaction. In alloantigen-induced immune responses, shuIL-1R suppresses lymphoproliferation and inflammation which result upon activation of T cells. shuIl-1R can therefore be used to effectively suppress alloantigen-induced immune responses in the clinical treatment of, for example, rejection of allografts (such as skin, kidney, and heart transplants), and graft-versus-host reactions in patients who have received bone marrow transplants.

shuIL-1R can also be used in clinical treatment of autoimmune dysfunctions, such as rheumatoid arthritis, diabetes and mutiple sclerosis, which are dependent upon the activation of T cells against antigens not recognized as being indigenous to the host.

Comparative Examples A–E below illustrate the use of soluble murine IL-1 receptor (smuIL-1R) in the in vivo treatment of various immune and inflammatory responses in mice. Murine IL-1R binds and transduces the biological signal provided by the IL-1 molecule in mice and shares significant amino acid sequence similarity with human IL-1R. In fact, murine IL-1 receptor binds to the human IL-1 with a greater affinity than human IL-1 receptor. Human IL-1 receptor also binds to murine IL-1. Because murine and human IL-1 receptors bind to each others' ligand and have similar biological functions in the murine and human immune systems, the in vivo activity of soluble murine IL-1 receptor in mice is indicative of the expected activity of soluble human IL-1 receptor in humans. The following examples are therefore evidence of the in vivo therapeutic utility of soluble IL-1 receptor in humans.

COMPARATIVE EXAMPLES

Example A

Use of smuIL-1R to Suppress Immune Response to Alloantigen In Vivo

Experiments were conducted to show that systemic administration of smuIL-1R suppresses a localized, T cell-dependent, immune response to alloantigen presented by allogeneic cells. The response to allogeneic cells in vivo was quantified using the popliteal lymph node enlargement assay described by Twist et al., *Transplantation* 15: 182, 1973, which is used as a measure of allograft transplant immunity (see Grebe et al., *Adv. Immunol.* 22:119, 1976). Cells from alloreactive lymph nodes were also examined to determine the phenotypes. Finally, cells from alloreactive nodes were examined for evidence of specific sensitization to the allogeneic cells used to induce the response.

1. Determination of Alloreactivity by Lymph Node Weight Gain. In this assay mice are injected in the footpad with irradiated, allogeneic spleen cells. The mice are then injected in the contralateral footpad with irradiated, syngeneic spleen cells. An alloreactive response (marked by proliferation of lymphocytes and inflammation) occurs in the footpad receiving the allogeneic cells, which can be measured by determining the increase in size and weight of the popliteal lymph node draining the site of antigen deposition relative to controls or by an increase in cellularity.

Specific pathogen free 8-12 week old BALB/c ($H-2^d$) and C57BL/6 ($H-2^b$) mice (Jackson Laboratory, Bar Harbor, ME) were used in this experiment. 48 BALB/c mice were divided into 16 groups, each having 3 mice (unless otherwise indicated). Each group of mice received a different mode of treatment as indicated below in Tables A-D. On day 0 the left footpads of all mice were injected intracutaneously with $10^7$ irradiated (2500R), allogeneic spleen cells from C57BL/6 mice in 50 ul of RPMI-1640 (Gibco) as antigen and the right contralateral footpads of the same mice were injected with $10^7$ irradiated (2500R), syngeneic spleen cells from BALB/c mice. Mice treated with smuIL-1R received smuIL-1R (expressed and purified as described by Dower et al., *J. Immunol.* 142:4314, 1989) together with 100 ng of mouse serum albumin (MSA) (Sigma, St. Louis, Mo.) by intraperitoneal injections on days $-1$ and 0, and by subcutaneous injections on days $+1$ and $+2$, relative to antigen administration, unless otherwise noted. smuIL-1R was diluted in MSA to the appropriate concentration prior to injection. The diluted receptor preparation always resulted in less than 20 pg of LPS endotoxin being delivered per treatment as measured by the Limulus amebocyte assay (M.A. Bioproducts). Control mice received MSA but no smuIL-1R.

Seven days after antigen administration, the mice were sacrified and the popliteal lymph nodes (PLN) were removed from the right and left popliteal fossa by surgical dissection. Lymph nodes were weighed and the results expressed as the difference ($\Delta$) in weight (mg) of the lymph node draining the site of allogeneic cell injection and the weight of the node draining the syngeneic cell injection site (Tables A and B; FIGS. 2A and 2B). Lymph nodes draining the syngeneic cell injection site weighed approximately 1 mg, regardless of whether they were obtained from mice treated with MSA or smuIL-1R, and did not differ significantly in weight from nodes obtained from mice given no cell injection. Values for statitical significance were calculated using the two-tailed Student's t-test. The p values reported in the tables represent the probability that $\Delta$ values obtained in experimental mice differ by chance alone from those in corresponding control mice. Lymph node weights reported as 0 have been normalized.

TABLE A

Effect of smuIL-1R Administration on Proliferation of Lymph Node Cells

| Treatment Group | Weight (mg) of Lymph Node | | |
|---|---|---|---|
| | Allogeneic | Syngeneic | $\Delta$ |
| MSA | 4.57 ± 0.22 | 1.7 ± 0.21 | 2.87 ± 0.38 |
| 1 μg smuIL-1R (2 mice) | 3.17 ± 0.61 | 2.1 ± 0.15 | 1.07 ± 0.6 ($p < 0.05$) |

TABLE A-continued

Effect of smuIL-1R Administration on Proliferation of Lymph Node Cells

| Treatment Group | Weight (mg) of Lymph Node | | |
|---|---|---|---|
| | Allogeneic | Syngeneic | $\Delta$ |
| 2 μg smuIL-1R | 2.83 ± 0.66 | 3.06 ± 0.6 | (0.00) ($p < 0.05$) |

TABLE B

Effect of smuIL-1R Administration on Proliferation of Lymph Node Cells

| Treatment Group (days treated) | Weight (mg) of Lymph Node | | |
|---|---|---|---|
| | Allogeneic | Syngeneic | $\Delta$ |
| MSA | 5.50 | 1.6 | 3.90 |
| | 5.00 | 1.3 | 3.70 |
| | 2.70 | 0.40 | 2.30 |
| | | | Average 3.3 ± 0.5 |
| 1 μg smuIL-1R (+1, +2, +3, +4) | 4.2 | 2.1 | 2.1 |
| | 5.2 | 1.6 | 3.6 |
| | 3.5 | 1.7 | 1.8 |
| | | | Average 2.5 ± 0.55 |
| 1 μg smuIL-1R (0, +1, +2, +3) | 3.4 | 1.8 | 1.6 |
| | 3.5 | 1.8 | 1.7 |
| | 4.3 | 2.0 | 2.3 |
| | | | Average 1.87 ± 0.21 ($p < 0.07$) |
| 1 μg smuIL-1R (−1, +0, +1, +2) | 2.7 | 0.8 | 1.9 |
| | 2.5 | 1.1 | 1.4 |
| | 1.2 | 0.9 | 0.3 |
| | | | Average 1.2 ± 0.47 ($p < 0.05$) |
| 2 μg smuIL-1R (−1, 0, +1, +2) | 1.2 | 1.00 | 0.2 |
| | 2.0 | 0.90 | 1.1 |
| | 2.1 | 1.40 | 0.7 |
| | | | Average 0.67 ± 0.26 ($p < 0.01$) |

Tables A and B (illustrated graphically in FIGS. 2A and 2B) show that systemic administration of sIL-1R for 3-4 days beginning on day $-1$ relative to alloantigenic challenge resulted in a dramatic decrease in the size of lymph nodes, indicating that the lymphoproliferative response is inhibited. The effect was dose dependent and, in some cases, the response was completely eliminated (Table A; FIG. 2A). Inhibition of the PLN response was also dependent on time of sIL-1R administration, with treatment starting one day prior to allogeneic cell challenge being the most effective (Table B; FIG. 2B). No significant inhibition was observed when treatment began one day after allogeneic cell challenge. Thus, IL-1R appears to interfere with an early event in the induction of the lymphoproliferative response.

To determine whether the effect of sIL-1R in the PLN system could be modified by administration of exogenous IL-1, mice were treated as above with sIL-1R and recombinant IL-1α administered separately (Table C; FIG. 2C) or administered together (either premixed prior to injection or injected separately at different sites) (Table D; FIG. 2D). Recombinant IL-1α was generated in *E. coli* and purified to homogeneity as described by Kronheim et al., *Bio/Technology* 4:1078, 1986.

TABLE C

Effect of IL-1α on smuIL-1R-Induced PLN Response

| Treatment Group | Weight (mg) of Lymph Node | | |
|---|---|---|---|
| | Allogeneic | Syngeneic | $\Delta$ |
| Untreated | 6.5 | 2.3 | 4.2 |
| | 6.7 | 2.8 | 3.9 |
| | | | Average 3.77 ± 0.3 |
| MSA | 7.3 | 1.9 | 5.8 |

TABLE C-continued

Effect of IL-1α on smuIL-1R-Induced PLN Response

| Treatment Group | Weight (mg) of Lymph Node | | |
|---|---|---|---|
| | Allogeneic | Syngeneic | Δ |
| | 5.2 | 1.6 | 3.6 |
| | 6.0 | 2.4 | 3.6 |
| | | | Average 4.33 ± 0.733 (p < 0.05) |
| IL-1α (100 ng) | 4.8 | 1.5 | 3.3 |
| | 6.3 | 1.6 | 4.7 |
| | 4.7 | 1.2 | 3.5 |
| | | | Average 3.83 ± 0.44 (0.00) |
| smuIL-1R (2 µg) | 2.0 | 2.9 | |
| | 3.9 | 2.1 | 1.8 |
| | 4.7 | 2.5 | 2.2 |
| | | | Average 1.03 ± 0.97 |

TABLE D

Effect of IL-1α on smuIL-1R-Induced PLN Response

| Treatment Group | Weight (mg) of Lymph Node | | |
|---|---|---|---|
| | Allogeneic | Syngeneic | Δ |
| MSA | 3.7 | 1.5 | 2.2 |
| | 4.6 | 2.0 | 2.6 |
| | 3.3 | 1.8 | 1.5 |
| | | | Average 2.1 ± 0.32 |
| IL-1/smuIL-1R (mixed prior to injection) | 4.7 | 2.2 | 2.5 |
| | 3.4 | 1.5 | 1.9 |
| | 5.1 | 2.0 | 3.1 |
| | | | Average 2.5 ± 0.34 |
| IL-1/smuIL-1R (injected separatedly) | 5.2 | 2.7 | 2.5 |
| | 5.1 | 2.8 | 2.3 |
| | 4.8 | 2.3 | 2.5 |
| | | | Average 2.47 ± 0.08 |
| smuIL-1R | 2.4 | 2.2 | 0.2 |
| | 3.2 | 2.4 | 0.8 |
| | 3.1 | 2.0 | 1.1 |
| | | | Average 0.67 ± 0.24 (p < 0.05) |

Table C (FIG. 2C) shows that administration of IL-1α alone had no effect on the PLN response. However, Table D (FIG. 2D) shows that when IL-1α was administered in conjunction with otherwise inhibitory doses of sIL-1R, the allogeneic PLN response was restored to that of MSA treated controls. The complete reversal of the inhibitory effect of sIL-1R by IL-1 strongly suggests that sIL-1R acts by virtue of its ability to neutralize IL-1.

2. Examination of Cell Phenotypes From Alloreactive Lymph Nodes. To investigate further the mechanism of action of sIL-1R on the PLN response, cells obtained from alloreactive nodes were examined to determine the prevalent surface phenotype of lymph node subpopulations, namely, whether the proliferating cells have surface Thy-1 molecules (CD4+ and CD8+) which are indicative of helper and suppressor T cell subsets or whether the cells have surface immunoglobulin (sIgM+) which is indicative of B cells. Cell suspensions were prepared from the draining lymph nodes of treated mice and resuspended in PBS containing 1% FBS and 0.1% NaN$_3$ for analysis by flow cytometry. Appropriate antibodies were bound to the cells by incubating 0.5 to $1 \times 10^6$ cells with optimal concentrations of antibody for 30 minutes at 4° C. and then washing three times. The monoclonal antibody reagents utilized were anti-mouse CD4 (anti-L3T4, clone GK1.5) conjugated to phycoerythrin and anti-mouse CD8 (anti-Lyt2, clone 53-6) conjugated to FITC (Becton Dickinson). Affinity purified goat F(ab')$_2$ anti-IgM (u chain specific, Tago) was utilized to detect B cells. Single color immunofluorescence analysis was performed with a FACScan (Becton Dickinson) flow cytometer. Cells not incubated with fluorochrome conjugated antibodies were analyzed to determine light scattering characteristics and autofluorescence levels. Nodes draining the site of syngeneic cell injection were pooled from two mice. Data for the nodes draining the site of allogeneic cell injection are from individual mice.

TABLE E

Effect of smuIL-1R Administration on Surface Phenotype of Lymph Node Populations

| Treatment Group | Cells Injected | Cells/Node × $10^{-6}$ | | | |
|---|---|---|---|---|---|
| | | CD4+ | CD8+ | sIgM+ | Total Cellularity |
| MSA | Syngeneic | 0.80 | 0.21 | 0.32 | 1.5 |
| sMuIL-1R | Syngeneic | 1.45 | 0.48 | 0.68 | 2.6 |
| MSA | Allogeneic | 2.85 | 0.88 | 5.25 | 9.4 |
| | | 3.00 | 0.76 | 3.90 | 8.3 |
| sMuIL-1R | Allogeneic | 1.28 | 0.31 | 1.11 | 3.0 |
| | | 1.46 | 0.37 | 1.18 | 3.3 |

Although the initiation of the PLN response depends on the presence of T cells in the host, Table E show that the actual cellular increase in the node occurs in both T cell and B cell compartments. Among T cells, both CD4+ and CD8+ cells are affected. sIL-1R treatment interferred with increases in all lymphoid subsets in the draining lymph node as defined by these markers.

3. T Cell Sensitization to Alloantigens in Lymph Nodes. Cells obtained from alloreactive nodes were also examined for evidence of specific sensitization to the allogeneic cells used to induce the response. To determine whether T cell sensitization to alloantigens had occurred in the lymph nodes of smuIL-1R treated mice, lymph node cell populations were tested for their capacity to respond in mixed leukocyte culture to the specific allogeneic cells used for sensitization and, as controls, to syngeneic cells and to third party allogeneic cells.

BALB/c mice (5 mice per group) were injected in one footpad with allogeneic (C57BL/6 or SJL) spleen cells and in the contralateral footpad pad with syngeneic (BALB/c) spleen cells that had been irradiated prior to injection. Recipients were treated with daily intraperitoneal injections of sIL-1R (2 mg) mixed with MSA (100 ng) or MSA alone on days −1, 0, and +1 relative to spleen cell injection. To determine whether cells in the lymph nodes were primed to allogeneic cells, mixed leukocyte cultures were established in 96-well microtiter plates by co-culturing $2 \times 10^5$ lymph node cells with $1 \times 10^6$ irradiated (2500R) C57BL/6, SJL or BALB/c spleen cells in triplicate. The culture medium was Dulbecco's Modified Eagle's Medium supplemented with 5% FBS, $5 \times 10^{-5}$M 2-mercaptoethanol and additional amino acids (Cerrottini et al., *J. Exp. Med.* 140: 703, 1974)). Cultures were pulsed overnight with $^3$H-TdR on day 3, 5 or 7 after culture initiation. Maximal proliferation occurred on day 5, the results of which are shown below in Table F. Nodes challenged with allogeneic cells of a particular type (C57BL/6 or SJL) were pooled from each group, as were nodes challenged with syngeneic cells, prior to cell harvest and culture. MSA-treated mice that received C57BL/6 or SJL spleen cells exhibited a PLN Δ value of 2.3±0.2 and 2.3±0.3 mg, respectively; smuIL-1R-treated mice that received C57BL/6 cells exhibited a PLN Δ value of 0.3±0.1 mg.

TABLE F

Effect of smuIL-1R Administration on In Vivo Priming to Alloeneic Cells in the Draining Lymph Node

| Treatment of BALB/c Host | Stimulating Cells | | cpm ± s. d. × $10^{-3}$ |
|---|---|---|---|
| | In Vivo | In Vitro | |
| MSA | C57BL/6 | C57BL/6 | 82.6 ± 6.7 |
| | | BALB/c | 1.2 ± 0.02 |
| | | SJL | 34.1 ± 6.0 |
| MSA | BALB/c | C57BL/6 | 43.3 ± 13.2 |
| | | BALB/c | 1.6 ± 0.5 |
| | | SJL | 31.7 ± 4.0 |
| MSA | SJL | C57BL/6 | 44.8 ± 2.9 |
| | | BALB/c | 1.3 ± 0.02 |
| | | SJL | 76.1 ± 3.8 |
| sIL-1R | C57BL/6 | C57BL/6 | 110.5 ± 16.9 |
| | | BALB/c | 1.3 ± 0.2 |
| | | SJL | 42.9 ± 3.6 |
| sIL-1R | BALB/c | C57BL/6 | 36.5 ± 5.3 |
| | | BALB/c | 1.4 ± 0.4 |
| | | SJL | 20.8 ± 1.4 |
| None | None | C57BL/6 | 51.1 ± 4.8 |
| | | BALB/c | 1.8 ± 0.5 |
| | | SJL | 40.3 ± 6.2 |

Table F shows that cells obtained from BALB/c popliteal lymph nodes draining the C57BL/6 cell injection site proliferated to a higher degree in response to in vitro challenge with the immunizing C57BL/6 cells than did (1) cells obtained from nodes of the same mice which drain the site of injection of syngeneic cells or (2) cells from unprimed mice. The secondary-type response, characteristic of sensitized T cells, occurred regardless of whether mice were injected with sIL-1R or MSA. The response was specific for cells from the C57BL/6 immunizing strain, as the response of the same cells to third party SJL stimulating cells was identical to the primary response of cells from non-immunized mice. Thus, although smuIL-1R administration significantly decreases the size of lymph nodes draining the allogeneic cell injection site, the cell populations that are present in such nodes contain specifically sensitized cells. This data indicates that sIL-1R modulates the allogeneic response in vivo not by interfering with T cell recognition and sensitization per se, but possibly by perturbing subsequent processes, such as secretion of other cytokines, which normally serve to amplify the immune response. Alternatively, sIL-1R may block the allogeneic response independently of T cell involvement, by precluding induction of the inflammatory events normally triggered by IL-1.

These results demonstrate that smuIL-1R is capable of suppressing immune responses to alloantigen upon exogeneous administration in vivo. Specifically, administration of smuIL-1R suppresses proliferation of lymphocytes and inflammation. The ability of smuIL-1R to act as a neutralizing agent for the endogeneously produced IL-1 ligand in mice is evidence of its therapeutic potential in the treatment of a variety of human clinical disorders associated with alloantigen-induced immune activities.

Example B

Use of smuIL-1R to Suppress Allograft Rejection smuIL-1R also suppresses rejection of organ grafts in vivo. In order to demonstrate this, neonatal C57BL/6 (H-$2^b$) hearts were transplanted into the ear pinnae of adult BALB/c (H-$2^d$) recipients utilizing the method of Fulmer et al., *Am. J. Anat.* 113:273, 1963, modified as described by Trager et al., *Transplantation* 47:587, 1989, and Van Buren et al., *Transplant. Proc.* 15:2967, 1983.

Survival of the transplanted hearts was assessed by visually inspecting the grafts for pulsatile activity. Pulsatile activity was determined by examining the ear-heart grafts of anesthetized recipients under a dissecting microscope with soft reflected light beginning on day 5 or 6 post transplant. The time of graft rejection was defined as the day after transplantation on which contractile activity ceases.

Recipient mice were transplanted on day 0 and injected with either smuIL-1R (2 ug/day) plus MSA (mouse serum albumin, 100 ng) or with MSA alone on days 0 through 6, alternating i.p. and s.c. routes. In a second heart transplant experiment, the mice were injected with MSA alone on days 0 through 2, i.p. route only. The results of this experiment are reported below in Example G. The probability that the survival time for the group treated with smuIL-1R differs by chance alone from the group treated with MSA is <0.03 when analyzed by the Wilcoxon Rank Sum test and <0.001 when analyzed by the Student's t-test for experiment 1. The corresponding values for experiment 2 are, respectively, p<0.06 and p<0.003.

TABLE G

Effects of smuIL-1R Treatment on Nonvascularized Heterotopic Cardiac Allograft Survival

| Treatment Group | Survival Time (days) | Median Survival Time ± S. D. |
|---|---|---|
| Experiment 1 | | |
| MSA | 12, 12, 12, 12, 13, 13, 13 | 12.5 ± 0.55 |
| smuIL-1R | 14, 16, 17, 17, 17, 20, 21 | 17 ± 2.4 |
| Experiment 2 | | |
| MSA | 11, 13, 13, 13 | 12 ± 1.0 |
| smuIL-1R | 17, 17, 19, 20 | 18 ± 1.5 |

Table G shows that heart allografts survived 11-13 days in individual control mice treated with MSA. When allograft recipients were given three to six daily injections of smuIL-1R, graft survival was prolonged in every case. The median graft survival time in smuIL-1R treated mice (17-18 days) was five to six days longer than the survival time of identical grafts in control mice. The prolongation of cardiac allograft survival achieved with this short course treatment of smuIL-1R is similar to or greater than that observed with other immunosuppressive regimens, such as anti-CD4 antibody treatment or total lymphoid irradiation (Trager et al., *Transplantation* 47:587, 1989). This data is evidence of the therapeutic potential of soluble human IL-1 receptor in humans for the suppression of heart allograft rejection.

Example C

Local Administration (IA) of smuIL-1R to Suppress Inflammatory Arthritis sIL-1R is also useful for the suppression of inflammatory arthritis. In order to determine the effect of sIL-1R on inflammatory arthritis, chronic synovitis was experimentally induced by intra-articular (IA) injection of soluble antigenic proteins, e.g., egg albumin or bovine serum albumin, in animals previously rendered immune to the injected protein. smuIL-1R was then injected into the patient to suppress inflammation. Due to similarities in histological characteristics and chronicity, antigen-induced arthritis (AIA) in animals has been used as an experimental model for human rheumatoid arthritis.

30 rats were divided into 6 groups, designated Groups A-F, each having 5 rats. All groups were immunized by subcutaneous injection of methylated bovine serum albumin (mBSA). For each immunization, 1 mg mBSA was emulsified in complete Freunds adjuvant (CFA) in a volume of 0.4 ml and injected in 0.2 ml doses into two flank sites.

On day 21 following immunization with mBSA, an AIA response was elicited in both hind knee joints of the rats by injecting the joints intra-articularly (IA) with 50 ug mBSA in a 10 ul volume while anesthetized with ether using a 30 gauge needle on a tuberculin syringe and a Tridak stepper set at a 10 ul volume. On the same day, the left hind knee joints of Groups A-C were similarly injected with saline as a negative control and the right contralateral hind knee joints were injected with IL-1α (100 ng, 10 ng or 1 ng, respectively) as a positive control. The left hind knee joints of Groups D, E and F were injected with saline as a negative control and the right contralateral hind knee joints were injected with smuIL-1R (1000 ng, 100 ng or 10 ng, respectively). The diameter of the largest region of the treated joints is measured using a caliper on days 2, 4, 6 and 8 relative to day 0 intra-articular injection of antigen. The results of these experiments are shown in Tables H and I and are graphically illustrated in FIGS. 3A-3C.

TABLE H

Joint Inflammation Induced by Intra-Articular Antigen Following Intra-Articular Treatment with IL-1α on Day 0

| Days After AIA | Joint Diameter (mm) Treatment with IL-1α or saline control | | | | | |
|---|---|---|---|---|---|---|
| | 1 ng | Saline | 10 ng | Saline | 100 ng | Saline |
| 2 | 8.2 ± 0.1 | 8.0 ± 0.1 | 8.2 ± 0.1 | 8.4 ± 0.1 | 8.0 ± 0.2 | 8.8 ± 0.2 |
| 4 | 7.7 ± 0.1 | 8.5 ± 0.1 | 7.4 ± 0.3 | 8.2 ± 0.1 | 7.4 ± 0.1 | 8.4 ± 0.1 |
| 6 | 6.2 ± 0.4 | 8.6 ± 0.1 | 6.0 ± 0.2 | 8.2 ± 0.1 | 5.8 ± 0.2 | 8.3 ± 0.2 |
| 8 | 6.0 ± 0.1 | 8.2 ± 0.3 | 6.0 ± 0.2 | 7.5 ± 0.3 | 5.6 ± 0.1 | 8.6 ± 0.2 |

TABLE I

Joint Inflammation Induced by Intra-Articular Antigen Following Local (IA) Treatment with smuIL-1R on Day 0

| Days After AIA | Joint Diameter (mm) Treatment with smuIL-1R or saline control | | | | | |
|---|---|---|---|---|---|---|
| | 10 ng | Saline | 100 ng | Saline | 1000 ng | Saline |
| 2 | 8.1 ± 0.1 | 8.2 ± 0.1 | 7.9 ± 0.2 | 7.9 ± 0.2 | 7.6 ± 0.1 | 8.3 ± 0.1 |
| 4 | 8.1 ± 0.2 | 8.4 ± 0.1 | 7.7 ± 0.2 | 8.6 ± 0.2 | 7.9 ± 0.1 | 7.9 ± 0.2 |
| 6 | 7.7 ± 0.4 | 8.5 ± 0.1 | 6.9 ± 0.4 | 7.2 ± 0.5 | 6.8 ± 0.2 | 6.7 ± 0.5 |
| 8 | 6.9 ± 0.3 | 8.3 ± 0.1 | 7.0 ± 0.6 | 7.7 ± 0.5 | 5.9 ± 0.1 | 6.4 ± 0.5 |

Table H (positive control) shows that IL-1α significantly reduced joint swelling in the AIA model at all doses. Table I shows that smuIL-1R significantly reduced joint swelling at doses of 1000 ng, but not at doses of 100 ng and 10 ng. The foregoing data indicates a correlation of reduced joint inflammation with intra-articular (local) administration of smuIL-1R at doses of 1000 ng on the day of injection of antigen. In addition, local administration of smuIL-1R by intra-articular injection appeared to have a systemic effect at the 1000 ng dose level, as indicated by the reduction in joint swelling in the contralateral footpad over the period of treatment. This suggests that systemic administration of sIL-1R may be effective in reducing AIA. The data also suggest that lower doses administered over a longer period of time may be effective.

Example D

Systemic Administration (RO) of smuIL-1R to Suppress Inflammatory Arthritis 20 rats are divided into 4 groups, designated Groups G-J, each having 5 rats. All rats are immunized by subcutaneous injection as described in Example C above.

On day 21 following immunization with mBSA, an AIA response was elicited was described in Example C above. On the same day, Group G was injected retroorbitally (RO) with a 0.2 ml volume of saline as a negative control. Groups H and I were injected RO with a 0.2 ml volume of smuIL-1R (0.1 ug and 1 ug, respectively) and Group J was injected RO with a 0.2 ml volume of IL-1α (10 ug) as a positive control.

The diameter of the largest region of the treated joints is measured using a caliper on days 2, 4, 6 and 8 relative to day 0 intra-articular injection of antigen. The results of these experiments are shown in Table J and are graphically illustrated in FIGS. 4A-4C.

TABLE J

Joint Inflammation Induced by Intra-Articular Antigen Following Systemic (RO) Treatment with smuIL-1R on Day 0

| Days After AIA | Joint Diameter (mm) | | | |
|---|---|---|---|---|
| | Saline Treatment | Treatment with smuIL-1r | | |
| | | 10 ng | 1 ng | 0.1 ng |
| 0 | 4.3 ± 0.1 | 4.2 ± 0.1 | 4.3 ± 0.1 | 4.2 ± 0.1 |
| 1 | 7.9 ± 0.2 | 7.4 ± 0.1 | 7.2 ± 0.1 | 7.6 ± 0.1 |
| 2 | 7.7 ± 0.1 | 7.8 ± 0.1 | 7.2 ± 0.1 | 7.7 ± 0.1 |
| 3 | 8.4 ± 0.1 | 7.5 ± 0.1 | 8.6 ± 0.1 | 7.8 ± 0.1 |
| 4 | 8.5 ± 0.1 | 7.7 ± 0.2 | 7.8 ± 0.2 | 8.2 ± 0.1 |
| 5 | 8.1 ± 0.2 | 7.5 ± 0.2 | 7.6 ± 0.3 | 7.7 ± 0.2 |
| 6 | 7.7 ± 0.3 | 7.5 ± 0.3 | 7.4 ± 0.3 | 7.6 ± 0.3 |
| 7 | 7.2 ± 0.3 | 7.5 ± 0.3 | 6.8 ± 0.2 | 7.3 ± 0.2 |

The foregoing measurements indicated a correlation of reduced joint inflammation with retroorbital (systemic) administration of 10 ug of smuIL-1R on the day of injection of antigen. The lower doses of smuIL-1R (1 ug and 0.1 ug) did not show significant reduction in knee joint swelling, possibly because the mode of administration requires either larger or more frequent dosages of smuIL-1R. Higher doses (e.g., 100 ng) or more frequent or earlier administration (e.g., on days −1, 0 and +1) would be expected to show greater reduction in knee joint swelling.

Example E

Systemic Administration (IP) of smuIL-1R to Suppress Inflammatory Arthritis 25 rats are divided into 5 groups, designated Groups K-O, each having 5 rats. All rats are immunized by subcutaneous injection as described in Example C above.

On day 21 following immunization with mBSA, an AIA response is elicted as described in example C. On days −1, 0 and +1 relative to injection of antigen, Group K was injected intraperitoneally (IP) with a 0.4 ml volume of saline as a negative control, Group L was injected IP with a 0.4 ml volume of IL-1α (0.1 ug) as a positive control and Groups M, N and O were injected IP with a 0.4 ml volume of smuIL-1R (0.1 ug, 1 ug and 10 ug, respectively).

The diameter of the largest region of the treated joints is measured using a caliper on days 2, 4, 6 and 8 relative to day 0 intra-articular injection of antigen. The results of these experiments are shown in Table K and are graphically illustrated in FIGS. 5A-5D.

TABLE K

Joint Inflammation Induced by Intra-Articular Antigen Following Systemic (IP) Treatment with smuIL-1R or IL-1α on Days −1, 0 and +1

| Days After AIA | Joint Diameter (mm) Treatment | | | | |
|---|---|---|---|---|---|
| | Saline | IL-1α | smuIL-1R | | |
| | 10 µg | 0.1 µg | 10 µg | 1 µg | 0.1 µg |
| 0 | 4.6 ± 0.1 | 4.7 ± 0.1 | 4.6 ± 0.1 | 4.7 ± 0.1 | 4.7 ± 0.1 |
| 1 | 7.0 ± 0.2 | 7.2 ± 0.1 | 7.0 ± 0.1 | 7.0 ± 0.1 | 7.0 ± 0.1 |
| 2 | 9.0 ± 0.2 | 8.0 ± 0.2 | 8.9 ± 0.1 | 8.5 ± 0.1 | 8.3 ± 0.2 |
| 3 | 9.2 ± 0.1 | 8.6 ± 0.1 | 8.7 ± 0.1 | 8.7 ± 0.1 | 8.7 ± 0.1 |
| 4 | 9.0 ± 0.1 | 8.3 ± 0.2 | 8.7 ± 0.2 | 8.6 ± 0.1 | 8.8 ± 0.2 |
| 5 | 9.1 ± 0.1 | 7.8 ± 0.2 | 8.2 ± 0.2 | 8.4 ± 0.2 | 9.0 ± 0.1 |
| 6 | 8.7 ± 0.1 | 7.8 ± 0.2 | 8.3 ± 0.3 | 8.1 ± 0.2 | 8.6 ± 0.2 |
| 7 | 8.4 ± 0.2 | 7.6 ± 0.2 | 8.2 ± 0.3 | 8.2 ± 0.2 | 8.4 ± 0.2 |
| 8 | 8.5 ± 0.2 | 7.5 ± 0.2 | 8.2 ± 0.3 | 7.9 ± 0.2 | 8.3 ± 0.2 |

The foregoing measurements indicate a correlation of reduced joint inflammation with intraperitoneal (systemic) administration of smuIL-1R on days −1, 0 and +1 relative to the day of antigen injection. In particular, the above data shows that increased frequency of systemic (IP) administration over a three day period of time is more effective than a single systemic (RO) administration (see Table J).

Examples 1–4, below, illustrate various aspects of the construction, expression and purification of soluble human IL-1 receptor. Example 5 illustrates the use of soluble human IL-1 receptor in the PLN assay (as described in Comparative Example A). These examples illustrate particular aspects of the present invention and are offered by way of illustration, and not by way of limitation.

EXAMPLES

Example 1

Construction, Expression and Purification of Soluble Truncated Recombinant Human IL-1 Receptor An expression construct for sHuIL-1R was generated in a series of steps as follows. A human IL-1 receptor cDNA fragment containing nucleotide sequences from the extracellular region of human IL-1R (see Sims et al., Proc. Natl. Acad. Sci. (USA), 86:8946, 1989) was first cleaved in 5' of the initiator methionine with the restriction enzyme StyI, and blunt ended using the T4 polymerase reaction method of Maniatas et al., Molecular Cloning: A Laboratory Manual, Cold Spring Harbor, p. 118, 1982.

The nucleotide sequences encoding the transmembrane and cytoplasmic regions of the resulting StyI digested human IL-1R cDNA fragment were then removed by cleavage with the restriction enzyme BbvI 32 base pairs 5' of the transmembrane region. The resulting cDNA fragment thus contained part of the 5' untranslated region and only a part of the coding region for the extracellular domain of the human IL-1R.

A portion of extracellular region deleted with the BbvI restriction enzyme was regenerated by synthesizing the following oligonucleotide:

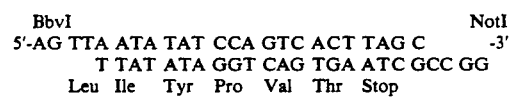

```
BbvI                                          NotI
5'-AG TTA ATA TAT CCA GTC ACT TAG C      -3'
      T TAT ATA GGT CAG TGA ATC GCC GG
      Leu Ile Tyr Pro Val Thr Stop
```

The expression vector into which the above IL-1R cDNA fragment and oligonucleotide were ligated was pDC205, which was derived from pMLSV, previously described by Cosman et al., Nature 312:768, 1984. pDC205 is designed to express cDNA sequences inserted at its multiple cloning site (MCS) when transfected into mammalian cells and includes the following components, in order of transcription from the early promoter: SV40 sequences from coordinates 5171–5270 containing the origin of replication, enhancer sequences and early and late promoters; adenovirus-2 sequences from coordinates 5779–6079 (containing sequences for the major late promoter and the first exon of the tripartite leader with the donor splice site removed), 7101–7172 and 9634–9693 (containing the second exon, with the acceptor splice site of the second exon of the tripartite leader removed, and part of the third exon of the tripartite leader); a multiple cloning site (MCS) containing sites for SmaI, NotI and BglII; a polyadenylation signal (pA) which contains SV40 sequences from coordinates 4127–4100 and 2770–2533 (containing the polyadenylation and termination signals for early transcription); adenovirus-2 sequences from coordinates 10535–11166 of the virus-associated RNA genes (VAI and VAII); and pBR322 sequences from coordinates 29–23, 4363–2486 and 1094–375 (containing the ampicillin resistance gene).

pDC205 was cleaved with the restriction enzyme Asp718, which was then blunt ended using the T4 polymerase reaction of Maniatas et al. (supra), and cleaved at the multiple cloning site with the restriction enzyme NotI.

The final step in the construction of a plasmid vector for expressing sHuIL-1R was the three-way ligation of (1) the StyI(blunt-ended)-BbvI cDNA fragment containing part of the 5' untranslated region and the insert encoding the extracellular domain of the human IL-1R, (2) the BbvI-NotI oligonucleotide fragment for regenerating the remaining extracellular domain of the human IL-1R, and (3) the NotI-Asp718 (blunt-ended) fragment comprising the expression vector pDC205.

To express recombinant sHuIL-1R, COS cells were grown and transfected as described by Cosman et al., supra, with the plasmid DNA from a 1.5 ml culture of E. coli transformed with pDC205 having a sIL-1R cDNA insert. After 72 hours of culture cells were harvested by washing once with 10 ml of PBS and then treating for 20 minutes at 37° C. with an EDTA solution (sodium phosphate 0.05M, sodium chloride 0.15M, EDTA 0.005M, pH 7.4) followed by scraping. For comparisons, COS cells were transfected with a pDC201 control vector containing no insert, and EL-4

6.1 C10 cells and EL-4M cells (an IL-1 receptor-negative variant of EL-4 cells) were grown and harvested as described by McDonald et al., *J. Immunol.* 135:3964 (1985).

The DNA encoding shuIL-1R replicates to a very high copy number when transfected into COS cells as described above. The high copy number allows efficient transcription of the IL-1 receptor DNA, thereby providing a high quantity of soluble IL-1 receptor for further study.

EXAMPLE 2

Expression of shuIL-1R in NS1 Cells

Recombinant shuIL-1R was expressed in the murine myeloma cell NS1 (ATCC TIB 18) as follows. First, an intermediate vector psfCA Vneo-S was derived from pDC201 (a derivative of pMLSV, previously described by Cosman et al., *Nature* 312: 768, 1984). psfCA Vneo-S comprises, in sequence with the direction of transcription from the origin of replication: (1) SV40 sequences from coordinates 5171–5270 containing the origin of replication, enhancer sequences and early and late promoters; (2) cytomegalovirus sequences containing the promoter and enhancer regions (nucleotides 671 to +63 from the sequence published by Boechart et al., *Cell* 41:521, 1985); (3) adenovirus-2 sequences from coordinates 5779–6079 containing sequences for the first exon of the tripartite leader (TPL), coordinates 7101–7172 and 9634–9693 containing the second exon and part of the third exon of the TPL and a multiple cloning site (MCS) containing sites for XhoI, KpnI, SmaI and BglII; (4) a nucleotide fragment containing the Neo$^r$ selective marker (for resistance to antibiotic G418) which was derived from a BglII-Sma fragment of pSV2neo (Southern and Berg, *J. Mol. Appl. Genet.* 1:327, 1982; ATCC No. 37149); (5) SV40 sequences from coordinates 4127–4100 and 2770–2533 containing the polyadenylation and termination signals for early transcription; (6) adenovirus sequences from coordinates 10535–11166 of the virus-associated RNA genes VAI and VAII of pDC201; (7) a 323 bp PvuII-StuI fragment (from coordinates 270–5190) from SV40 containing duplicate sequences of the SV40 origin of replication, enhancer sequences and early and late promoters; and (8) pBR322 sequences from coordinates 4363–2486 and 1094–375 containing the ampicillin resistance gene and origin of replication.

To create a vector for expression in NS1 cells, psfCA Vneo-S was combined in vitro with the plasmid pSV3dhfr (Subramani, Mulligan and Berg, *Molec. Cell. Biol.* 1:854, 1981; ATCC No. 37150). pSV3dhfr contains the DHFR+ genetic marker which codes for the essential enzyme dihydrofolate reductase and confers selective advantage to DHFR− mammalian cells lines grown in the presence of methotrexate (MTX). The DHFR+ genetic marker on pSV3dhfr is flanked by duplicate SV40 sequences containing the SV40 origin of replication, enhancer sequences and early and late promoters. psfCA Vneo-S and pSV3dhfr were subjected to preparative digestion with the SfiI restriction enzyme, which cleaves the plasmids within the duplicate SV40 regions. The resulting DNA was electrophoresed on a preparative agarose gel to remove the fragments containing the *E. coli* origins of replication, portions of the SV40 vector control sequences and ampicillin resistance gene. The fragments containing the shuIL-1R cDNA and the DHFR gene were religated in a ratio of 10:1 to form concatameric DNA vectors ranging from 6 to 50 kb containing multiple fragments of the shuIL-1R cDNA and the DHFR gene. The concatameric DNA, designated psfCA Vneo dhfr/IL-1R, was incorporated into NS1 cells by electroporation at 300 volts at 960 microfarads.

After electroporation, the viable cells were grown devoid of selective agents for 48 hours. After 48 hours, 264 pools of transfected cells were generated by seeding 24-well plates at cell densisites ranging from 3,000 to 30,000 cells per well. G418 was then added to the medium at a concentration of 1.5 mg/ml. Cells resistant to G418 were selected for approximately 25 days, then bioassayed for secretion of soluble human IL-1 receptor into the culture supernatant fraction. 79 of the 264 pools contained cells resistant to G418. 17 of the 79 G418 resistant pools secreted shuIL-1R, as determined using the standard IL-1 binding assay for soluble IL-1 receptor described in Example 4.

The highest expressing clone from the G418 selection was then subjected to further selection regimes. The high shuIL-1R expressing clonal cell line was first isolated by the method of limiting dilution in 96-well plates. Clonal cells are then subjected to stepwise selection for methotrexate (MTX) resistance by exposing the cells to gradually increasing concentrations (70, 150, 300 and 500 nM) of MTX. MTX inhibits the essential enzyme dihydrofolate reductase (DHFR), resulting in the death of cells which express DHFR at normal levels. The rare surviving cells are those that have undergone changes resulting in elevated levels of secreted IL-1R protein. One mechanism may involve duplication of specific gene sequences encoding DHFR (as a result of gene amplification in the course of DNA replication and recombination events) and are capable of producing sufficiently large amounts of uninhibited DHFR enzyme to generate tetrahydrofolate for survival and growth of the cells. MTX selection and amplification of the DHFR gene also selects for and amplifies contiguous DNA sequences encoding shuIL-1R and thus achieves enhanced expression of shuIL-1R. Resulting pools of NS1 cells are capable of producing approximately 10 micrograms/million cells/day under unoptimized conditions. These pools of NS1 cells can be further selected to obtain cells capable of expressing shuIL-1R in higher quantities.

The NS1 cells selected using the above protocol may be cultured in a bioreactor and used as a source of product suitable for human clinical therapy. NS1 cells transfected with soluble human IL-1 receptor cDNA are cultured in serum-free media composition such as that described by Kawamoto et al., *Anal. Biochem.* 130:445, 1983. Preferably the serum-free media is comprised of 100 parts by volume ABC protein-free media (ABC Enterprise, Inc.), 2 parts by volume TCM defined protein supplement (Celox Corp.) and a part by volume Ex-cyte VLE lipid mixture of cholesterol, phospholipid and fatty acids (Miles, Inc.).

EXAMPLE 3

Expression of Recombinant Soluble Human IL-1 Receptor in CHO Cells

Recombinant shuIL-1R was also expressed in a cell line generated from Chinese Hamster Ovary (CHO) cells. This variant cell line, designated CHO DG44, differs from the parental CHO cells principally in that it contains a chromosomal deletion of the endogenous DHFR gene.

The plasmids used to express shuIL-1R in this cell line were pDC205 and pGem7/DHFR. The shuIL-1R gene is under the control of the adenovirus 2 major late promoter of the plasmid pDC205, described above in Example 3. pGEM7/DHFR was constructed by inserting the DHFR gene into the multiple cloning site of the commercially available pGEM7 cloning vector (Promega Biotech, Madison, WI, USA) and the DHFR was used as a selectable gene.

The plasmid vectors pDC205 and pGEM7/DHFR were cotransfected into the CHO DG44 cells in a 10:1 molar ratio using a standard calcium phosphate transfection method, substantially as described by Ausubel et al., eds., *Current Protocols in Molecular Biology* (Green Publ. Assoc., Brooklyn, NY, USA), §9.1, 1989. A stable cell line expressing shuIL-1R was generated using the DHFR gene as a selective marker and high-copy-numbers of introduced shuIL-1R genes were produced through the use of a DHFR-amplification system as described by Simonsen et al., *Proc. Natl. Acad. Sci.* (USA) 80:2495, 1983. Briefly, after transfection, DHFR+ cells were selected by their ability to grow in $\alpha^-$ MEM selective media (Gibco) containing 5% dialyzed fetal calf serum, after which the cells were exposed to elevated levels of MTX (20 nM) to select for cells that express amplified levels of DHFR which are resistant to MTX. Cells surviving this level of MTX exposure were then cloned by limiting dilution and the resulting clonal cells which expressed shuIL-1R were identified by assaying for Il-1 binding as described in Example 1. Clones expressing the highest levels of shuIL-1R were then subjected to stepwise selection for MTX resistance by exposing the cells to gradually increasing concentrations (50, 200 and 800 nM) of MTX. MTX selection and amplification of the DHFR gene also selects for and amplifies contiguous DNA sequences encoding shuIL-1R and thus achieves enhanced expression of shuIL-1R. Pools from these selection regimes were determined to produce shuIL-1R at about 1 µg per million cells per day. Individual clones are then isolated by standard methods, such as limiting dilution cloning. Such clones can then be selected for MTX resistance at greater concentrations of MTX to obtain clones having higher expression of shuIL-1R.

EXAMPLE 4

Binding of shuIL-1R shuIL-1R produced according to Examples 2 and 3 was tested for its ability to bind IL-1 as follows. First, a non-blocking monoclonal antibody was generated to the human IL-1 receptor. A Lewis rat was boosted intradermally with $10^8$ pfu of recombinant human IL-1 receptor vaccinia virus. Three weeks later the rat was boosted with $10^6$ primary rat fibroblasts infected with vaccinia virus at greater than 5 pfu/cell. Two weeks later the rat was boosted intravenously with $2 \times 10^6$ C127 cells expressing recombinant human IL-1 receptor ($5 \times 10^5$ receptor/cell) (C127huIL1R). Three days after the intravenous boost the rat spleen cells were fused with X63-Ag8.653 murine myeloma cells. Hybridoma supernatants were screened for the capacity to react with C127 cell expressing human IL-R and not with parental C127 cells. One antibody (huIL-1Rm8) was further characterised as detecting human IL-1 receptor in a dot blot assay and as being capable of forming a complex with shuIL-1R that bound recombinant human $^{125}$I-IL-1$\alpha$ with an affinity identical to that of the full length form of the huIL-1R on cells. huIL-1Rm8 also does not inhibit binding of recombinant human $^{125}$I-IL-1$\alpha$ to cells. huIL-1Rm8 was determined to be a IgG$_{2b}$ by use of a Zymed isotyping kit.

To test the binding activity of the shuIL-1R ELISA plates were initially coated with soluble receptor alone. No IL-1 binding activity was detected. Subsequently shuIL1Rm8 (10 ug/ml final concentration in both cases, 50 ul/well) in PBS was incubated in the plates for 24 hours at 8° C., washed, reacted with truncated receptor (100 ng/ml final concentration) for 24 hours, at 8° C. $^{125}$I-IL-1$\alpha$ was added at varying concentrations. The binding of $^{125}$I-IL-1$\alpha$ to huIL-1Rm8/shuIL-1 receptor coated plates was dependent on the concentration of $^{125}$I-IL-1$\alpha$ added. The affinity ($7 \times 10^8$) is similar to that measured for full length receptor in the plasma membrane (Sims et al., *Proc. Natl. Acad. Sci.* (USA) 86:8946 1989). The shuIL-1R fragment retains the binding activity of the full length receptor.

EXAMPLE 5

Use of shuIL-1R to Suppress Immune Response to Alloantigen In vivo

Experiments were conducted to show that systemic administration of shuIL-1R suppresses a localized, T cell-dependent, immune response to alloantigen presented by allogeneic cells. In this experiment mice are injected in the footpad with irradiated, allogeneic spleen cells. The mice are then injected in the contralateral footpad with irradiated, syngeneic spleen cells. An alloreactive response (marked by proliferation of lymphocytes and inflammation) occurs in the footpad receiving the allogeneic cells, which can be measured by determining the increase in size and weight of the popliteal lymph node draining the site of antigen deposition relative to controls.

On day 0 twelve BALB/c mice were injected in the footpad with irradiated, allogeneic spleen cells from C57BL/6 mice and in the contralateral footpad with irradiated, syngeneic spleen cells from BALB/c mice. Three of the twelve mice were injected intraveneously on days −1 and 0, and +1 with 100 ng of purified shuIL-1R in phosphate buffered saline, three were injected intraveneously with 1 µg of shuIL-1R, three were injected intraveneously with 5 µg of sHuIL-1R and three were injected intraveneously with MSA (control). As set forth in Table 1 below, the mean difference in weight of the lymph nodes from the sites of allogeneic and syngeneic spleen cells was approximately 5.4 mg for the mice treated with MSA, approximately 5.6 mg for the mice treated with 100 ng of shuIL-1R (p=not significant), approximately 3.3 mg for mice treated with 1 µg shuIL-1R (p<0.2, not significant) and approximately 1.8 for the mice treated with 5 µg shuIL-1R. The weight of the syngeneic nodes did not differ significantly, ranging from about 1.93 mg on MSA treated mice to about 1.63 mg on mice treated with 5 µg of shuIL-1R. The third mouse treated at 100 ng died of an unknown cause after the first injection and was not therefore included in the statistical analysis. The dose of 5 µg shuIL-1R per mouse per day for 3 days inhibits popliteal lymph node hypertrophy by more than 50% (p<0.01 using the two-tailed T test). Thus, the dosage of 5 µg of shuIL-1R significantly suppresses the in vivo lymphoproliferative and inflammatory response in a dose dependent fashion relative to control mice.

TABLE 1

Effect of shuIL-1R Administration on
Proliferation of Lymph Node Cells

| Treatment | Weight (mg) of Lymph Node | | |
|---|---|---|---|
| | Allogeneic | Syngeneic | Δ |
| MSA | | | |
| 1 | 6.62 | 2.19 | 4.43 |
| 2 | 7.28 | 2.10 | 5.18 |
| 3 | 7.98 | 1.51 | 6.47 |
| Avg. | 7.29 ± 0.39 | 1.93 ± 0.2 | 5.36 ± 0.6 |
| 100 ng | | | |
| 1 | 8.44 | 2.08 | 6.36 |
| 2 | 6.94 | 1.86 | 5.08 |
| 3 | (not included) | | |
| Avg. | 7.69 ± 0.75 | 1.97 ± 0.11 | 5.7 ± 0.64 |
| 1000 ng | | | |
| 1 | 6.36 | 1.48 | 4.88 |
| 2 | 4.78 | 2.25 | 2.53 |
| 3 | 4.36 | 1.71 | 2.65 |
| Avg. | 5.2 ± 0.6 | 1.81 ± 0.22 | 3.35 ± 0.76 |
| 5000 ng | | | |
| 1 | 3.80 | 1.59 | 2.21 |
| 2 | 3.28 | 1.70 | 1.58 |
| 3 | 2.55 | 1.59 | 0.96 |
| Avg. | 3.21 ± 0.36 | 1.63 ± 0.04 | 1.58 ± 0.36 |

Figure 6:
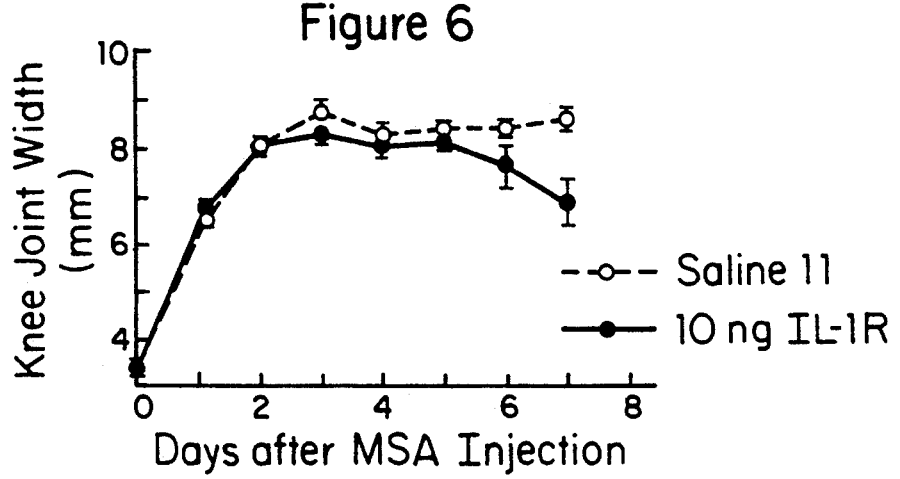
FIGS. 6A-6B are graphs showing that soluble human IL-1R inhibits alloantigen induced lymph node weight gain in mice.
Figure 7:
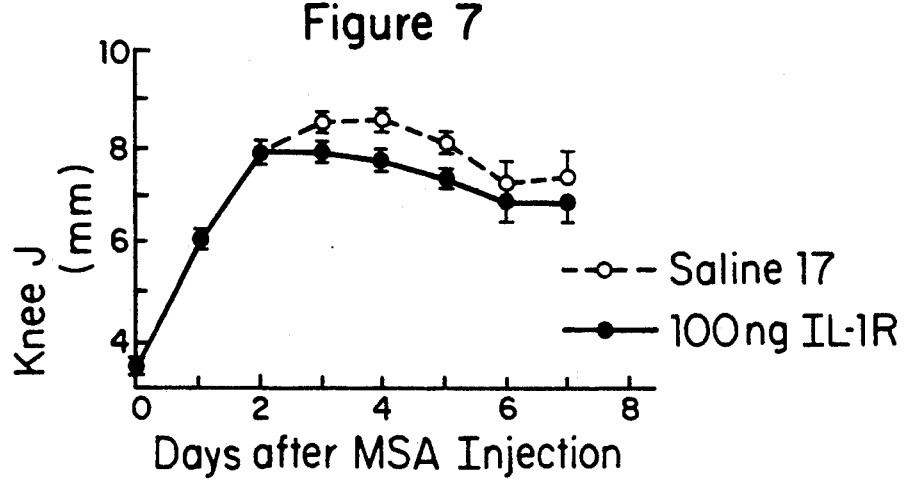
Figure 14:
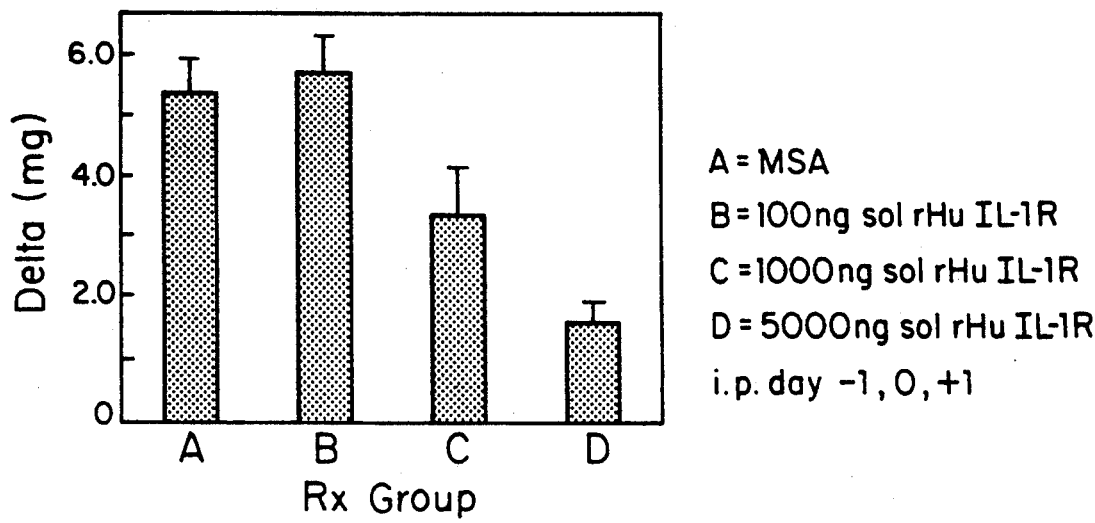
Figure 15:
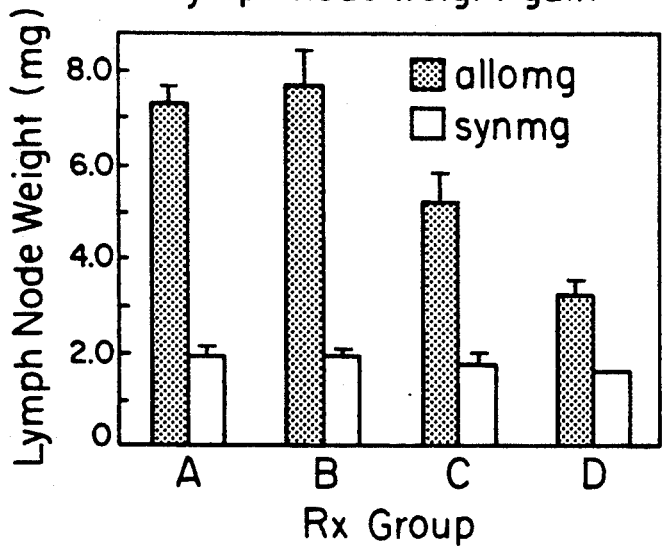

The results shown in Table 1 (and depicted graphically in FIGS. 6A and 6B) demonstrate that shuIL-1R is capable of suppressing immune responses to alloantigen upon exogeneous administration in vivo. Specifically, the data show that a dose of 5 ug/mouse/day for 3 days inhibits the PLN hypertrophy by more than 50%. This dose is 5-fold higher by weight than the amount of smuIL-1R required to produce the same level of inhibition as shown in Comparative Example A. The higher dose is most probably a result of the lower binding affinity of shuIL-1R for the murine IL-1 ligand. The ability of shuIL-1R to inhibit the activity of the endogeneously produced IL-1 ligand in mice is evidence not only of the cross reactivity of shuIL-1R and smuIL-1R in mice (and demonstrating that evidence of in vivo efficacy of muIL-1R is predictive of in vivo efficacy of hu IL-1R), but also of its therapeutic potential of shuIL-1R in the treatment of a variety of clinical disorders associated with alloantigen-induced immune activities in humans.

We claim:

1. A substantially pure and homogeneous soluble human IL-1 receptor (shuIL-1R) protein comprising a sequence of amino acids selected from the group consisting of amino acid sequences 1-318, 1-317, 1-316 and 1-315 of FIG. 1A-1B.

2. A pharmaceutical composition comprising a soluble human IL-1 receptor according to claim 1 and a suitable diluent or carrier.

* * * * *